United States Patent
Ries et al.

(10) Patent No.: US 6,838,565 B2
(45) Date of Patent: Jan. 4, 2005

(54) SUBSTITUTED BENZOIC ACID AMIDES, THEIR PREPARATION AND THEIR USE AS PHARMACEUTICAL COMPOSITIONS

(75) Inventors: Uwe Ries, Biberach (DE); Henning Priepke, Warthausen (DE); Wolfgang Wienen, Biberach/Rissegg (DE); Herbert Nar, Ochsenhausen (DE); Sandra Handschuh, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/624,025

(22) Filed: Jul. 21, 2003

(65) Prior Publication Data

US 2004/0138309 A1 Jul. 15, 2004

Related U.S. Application Data

(60) Provisional application No. 60/404,434, filed on Aug. 19, 2002.

(30) Foreign Application Priority Data

Jul. 26, 2002 (DE) .......................................... 102 34 058

(51) Int. Cl.$^7$ ....................... C07D 257/04; A61K 31/41
(52) U.S. Cl. ....................... 548/253; 548/538; 548/539; 548/518; 546/276.4; 514/381; 514/423; 514/340
(58) Field of Search ................................. 548/253, 538, 548/539, 518; 546/276.4; 514/381, 423, 340

(56) References Cited

U.S. PATENT DOCUMENTS

2002/0151534 A1  10/2002  Ries et al.

FOREIGN PATENT DOCUMENTS

WO  WO 01/56989 A2  *  8/2001

OTHER PUBLICATIONS

Copy International Search Report Reference #PCT/EP 03/07924, Nov. 2003.

* cited by examiner

Primary Examiner—Shailendra Kumar
(74) Attorney, Agent, or Firm—Robert P. Raymond; Alan R. Stempel; Mary-Ellen M. Devlin

(57) ABSTRACT

Carboxylic acid amides of general formula

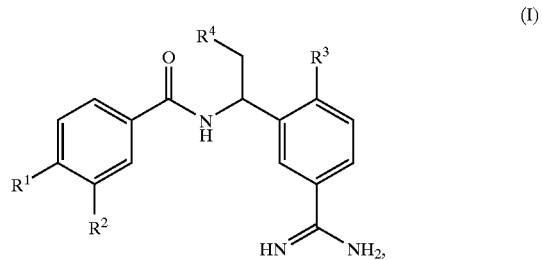

(I)

having an antithrombotic activity and a factor Xa-inhibiting activity. Exemplary are:

(a) N-[1-(3-amidino-phenyl)-2-(1H-tetrazol-5-yl)-ethyl]-4-(2,5-dihydro-pyrrol-1-yl-carbonyl)-3-methyl-benzamide, (b) N-[1-(3-amidino-phenyl)-2-(1H-tetrazol-5-yl)-ethyl]-3-methyl-4-(pyrrolidin-1-yl-carbonyl)-benzamide, (c) N-[1-(5-amidino-2-hydroxy-phenyl)-2-phenyl-ethyl]-3-methyl-4-(pyrrolidin-1-yl-carbonyl)-benzamide, and (d) N-[1-(5-amidino-2-hydroxy-phenyl)-2-(pyridin-3-yl)-ethyl]-3-methyl-4-(pyrrolidin-1-yl-carbonyl)-benzamide.

6 Claims, No Drawings

SUBSTITUTED BENZOIC ACID AMIDES, THEIR PREPARATION AND THEIR USE AS PHARMACEUTICAL COMPOSITIONS

RELATED APPLICATIONS

Benefit of U.S. Provisional Application Ser. No. 60/404,434, filed on Aug. 19, 2002 is hereby claimed.

FIELD OF THE INVENTION

The present invention relates to new benzoic acid amides of general formula

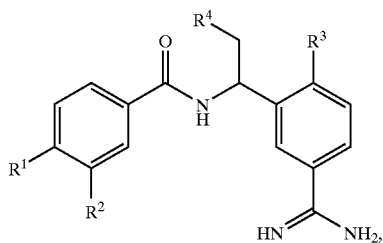

(I)

the tautomers, the enantiomers, the diastereomers, the mixtures and the salts thereof, particularly the physiologically acceptable salts thereof with inorganic or organic acids or bases, which have valuable properties.

The compounds of the above general formula I and the tautomers, the enantiomers, the diastereomers, the mixtures and the salts thereof, particularly the physiologically acceptable salts thereof with inorganic or organic acids or bases and the stereoisomers thereof, have valuable pharmacological properties, particularly an antithrombotic effect and a factor Xa-inhibiting effect.

Thus, the present application relates to the new compounds of the above general formula I, the preparation thereof, the pharmaceutical compositions containing the pharmacologically effective compounds, the preparation and use thereof.

In the above general formula $R^1$ denotes an amino, $C_{1-5}$-alkylamino, $C_{3-7}$-cycloalkylamino or (phenyl-$C_{1-3}$-alkyl)-amino group which may be substituted in each case at the amino-nitrogen atom by a phenylcarbonyl or phenylsulphonyl group or by a $C_{1-3}$-alkyl or $C_{1-3}$-alkyl-carbonyl group optionally substituted in the alkyl moiety by a carboxy group, a group which may be converted in-vivo into a carboxy group, an amino, $C_{1-3}$-alkylamino or di-($C_{1-3}$-alkyl)-amino group, while two nitrogen atoms are separated from each other by at least two carbon atoms, a di-($C_{1-5}$-alkyl)amino or N—($C_{3-7}$-cycloalkyl)-$C_{1-5}$-alkylamino group, while the $C_{1-5}$-alkyl moiety may be substituted in each case by a hydroxy, $C_{1-3}$-alkoxy, amino, $C_{1-3}$-alkyl-amino or di-($C_{1-3}$-alkyl)-amino group, with the exception of the 1 position, a 4- to 7-membered cycloalkyleneiminocarbonyl or cycloalkyleneiminosulphonyl group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylamino-carbonyl or di-($C_{1-3}$-alkyl)-aminocarbonyl group, a 2,5-dihydro-1H-pyrrol-1-yl-carbonyl group, an aminosulphonyl group optionally substituted by one or two $C_{1-3}$-alkyl groups, a $C_{3-7}$-cycloalkyl-carbonyl group, while the methylene group in the 3 or 4 position of a $C_{5-7}$-cycloalkyl-carbonyl group may be replaced by a —NH group wherein the hydrogen atom of the —NH group may be replaced by a $C_{1-3}$-alkyl or $C_{1-3}$-alkyl-carbonyl group, a phenylcarbonyl or heteroarylcarbonyl group, which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl or $C_{1-3}$-alkoxy group, or a group of formula

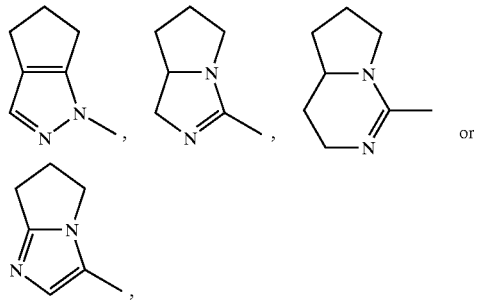

wherein in the heterocyclic moiety a hydrogen atom may be replaced by an aminomethyl or aminocarbonyl group in each case, $R^2$ denotes a hydrogen, fluorine, chlorine or bromine atom, a $C_{1-3}$-alkyl group wherein the hydrogen atoms may be wholly or partially replaced by fluorine atoms, a $C_{2-3}$-alkenyl, $C_{1-3}$-alkoxy or trifluoromethoxy group, $R^3$ denotes a hydrogen atom or a hydroxy or amino group and $R^4$ denotes a phenyl or heteroaryl group which is optionally substituted by a hydroxy, $C_{1-4}$-alkyloxy, benzyloxy, hydroxycarbonyl-$C_{1-3}$-alkoxy, $C_{1-3}$-alkyloxy-carbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, carboxy, $C_{1-3}$-alkyloxy-carbonyl group, a 1-H-pyridonyl or 1-($C_{1-3}$-alkyl)-pyridonyl group, a 4- to 7-membered cycloalkyleneimino group or a 4- to 7-membered cycloalkyl group wherein one or two methylene groups are replaced by an —NH or —N($C_{1-3}$-alkyl)-group and wherein one or two of the methylene groups adjacent to the —NH or —N($C_{1-3}$-alkyl)- group may each be replaced by a carbonyl group, with the proviso that a cycloalkyl group as hereinbefore defined wherein two —NH or —N($C_{1-3}$-alkyl)- groups are separated from one another by precisely one —CH$_2$— group is excluded, while, unless otherwise stated, the term heteroaryl group denotes a monocyclic 5- or 6-membered heteroaryl group optionally substituted in the carbon skeleton by a C$_{1-3}$-alkyl, carboxy, C$_{1-3}$-alkoxy-carbonyl or C$_{1-3}$-alkoxy-carbonylamino group, while the 6-membered heteroaryl group contains one, two or three nitrogen atoms and the 5-membered heteroaryl group contains an imino group optionally substituted by a C$_{1-3}$-alkyl or phenyl-C$_{1-3}$-alkyl group, an oxygen or sulphur atom or contains an imino group optionally substituted by a C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl or phenyl-C$_{1-3}$-alkyl group or an oxygen or sulphur atom and additionally contains a nitrogen atom or contains an imino group optionally substituted by a C$_{1-3}$-alkyl or phenyl-C$_{1-3}$-alkyl group and two or three nitrogen atoms, and moreover a phenyl ring may be fused to the abovementioned monocyclic heterocyclic groups via two adjacent carbon atoms and the binding takes place via a nitrogen atom or via a carbon atom of the heterocyclic moiety or a fused-on phenyl ring, while the amidino group contained in the compounds of general formula I may be substituted by a C$_{1-10}$-alkoxy-carbonyl, 2,2,2-trichloroethoxycarbonyl, phenyloxycarbonyl, benzyloxycarbonyl, phenylcarbonyl, hydroxy, C$_{1-5}$-alkyloxy, benzyloxy or phenyloxy group, and while the abovementioned alkyl and alkoxy groups include straight-chain and branched alkyl and alkoxy groups, wherein additionally one to 3 hydrogen atoms may be replaced by fluorine atoms.

By a group which can be converted in-vivo into a carboxy group is meant for example a carboxy group esterified with an alcohol wherein the alcoholic moiety is preferably a C$_{1-6}$-alkanol, a phenyl-C$_{1-3}$-alkanol, a C$_{3-9}$-cycloalkanol, a C$_{5-7}$-cycloalkenol, a C$_{3-5}$-alkenol, a phenyl-C$_{3-5}$-alkenol, a C$_{3-5}$-alkynol or phenyl-C$_{3-5}$-alkynol, with the proviso that no bond to the oxygen atom starts from a carbon atom which carries a double or triple bond, a C$_{3-8}$-cycloalkyl-C$_{1-3}$-alkanol or an alcohol of formula

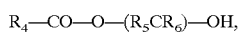

wherein

R$_4$ denotes a C$_{1-8}$-alkyl, C$_{5-7}$-cycloalkyl, phenyl or phenyl-C$_{1-3}$-alkyl group, R$_5$ denotes a hydrogen atom, a C$_{1-3}$-alkyl, C$_{5-7}$-cycloalkyl or phenyl group and R$_6$ denotes a hydrogen atom or a C$_{1-3}$-alkyl group.

Preferred groups which may be cleaved from a carboxy group in vivo include a C$_{1-6}$-alkoxy group such as the methoxy, ethoxy, n-propyloxy, isopropyloxy, n-butyloxy, n-pentyloxy, n-hexyloxy or cyclohexyloxy group or phenyl-C$_{1-3}$-alkoxy group such as the benzyloxy group.

Moreover, the above definition of the abovementioned saturated alkyl and alkoxy moieties which contain more than 2 carbon atoms, as well as alkanoyl and unsaturated alkyl moieties which contain more than 3 carbon atoms, also includes the branched isomers thereof such as for example the isopropyl, tertbutyl, isobutyl group, etc.

Those compounds of general formula I wherein R$^1$ to R$^4$ are as hereinbefore defined and wherein the amidino group is substituted by an aminomethyl group substituted by C$_{1-10}$-alkoxy-carbonyl, 2,2,2-trichloroethoxycarbonyl, phenyloxycarbonyl or benzyloxy-carbonyl group or by a C$_{1-10}$-alkoxy-carbonyl, 2,2,2-trichloroethoxycarbonyl, phenyloxy-carbonyl, benzyloxycarbonyl, phenylcarbonyl, hydroxy, C$_{1-5}$-alkyloxy, benzyloxy or phenyloxy group, are prodrugs for those compounds of general formula I which contain an unsubstituted amidino group.

Those compounds of general formula I wherein R$^1$ contains a group which may be converted in vivo into a carboxy group are prodrugs for those compounds of general formula I wherein R$^1$ contains a carboxy group.

Preferred compounds of the above general formula I are those wherein

R$^2$, R$^3$ and R$^4$ are as hereinbefore defined and

R$^1$ denotes a 4- to 7-membered cycloalkyleneimino-carbonyl group optionally substituted by a C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, aminocarbonyl, C$_{1-3}$-alkylamino-carbonyl or di-(C$_{1-3}$-alkyl)-aminocarbonyl group, a 2,5-dihydro-1H-pyrrol-1-ylcarbonyl group or a group of formula

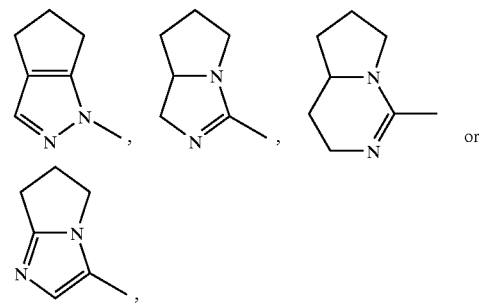

wherein in the heterocyclic moiety a hydrogen atom may be replaced in each case by an aminomethyl or aminocarbonyl group, while the amidino group contained in the compounds of general formula I may be substituted by a C$_{1-10}$-alkoxy-carbonyl, 2,2,2-trichloroethoxycarbonyl, phenyloxycarbonyl, benzyloxycarbonyl, phenylcarbonyl, hydroxy, C$_{1-5}$-alkyloxy, benzyloxy or phenyloxy group, the abovementioned alkyl and alkoxy groups including straight-chain and branched alkyl and alkoxy groups, wherein additionally one to 3 hydrogen atoms may be replaced by fluorine atoms, the tautomers, enantiomers, the diastereomers, the mixtures and the salts thereof.

Particularly preferred compounds of general formula I are those wherein

R$^1$, R$^2$ and R$^3$ are as hereinbefore defined and

R$^4$ denotes a phenyl, furanyl, thienyl, pyrrolyl, pyrazolyl, pyridinyl, pyrazinyl, pyridazinyl, pyrimidinyl, thiazolyl, tetrazolyl or isoxazolyl group which is optionally substituted by a hydroxy, C$_{1-4}$-alkyloxy, benzyloxy, hydroxycarbonyl-C$_{1-3}$-alkoxy, C$_{1-3}$-alkyloxy-carbonyl-C$_{1-3}$-alkyloxy, aminocarbonyl-C$_{1-3}$-alkyloxy, C$_{1-3}$-alkylaminocarbonyl-C$_{1-3}$-alkyloxy, di-(C$_{1-3}$-alkyl)-aminocarbonyl-C$_{1-3}$-alkyloxy, carboxy, C$_{1-3}$-alkyloxy-carbonyl group, while the amidino group contained in the compounds of general formula I may be substituted by a C$_{1-10}$-alkoxy-carbonyl, 2,2,2-trichloroethoxycarbonyl, phenyloxycarbonyl, benzyloxycarbonyl, phenylcarbonyl, hydroxy, C$_{1-5}$-alkyloxy, benzyloxy or phenyloxy group, the abovementioned alkyl and alkoxy groups including straight-chain and branched alkyl and alkoxy groups, wherein additionally one to 3 hydrogen atoms may be replaced by fluorine atoms, the tautomers, enantiomers, the mixtures and the salts thereof.

The following preferred compounds of general formula I are mentioned by way of example:

(1) N-[1-(3-amidino-phenyl)-2-(1H-tetrazol-5-yl)-ethyl]-4-(2,5-dihydro-pyrrol-1-yl-carbonyl)-3-methyl-benzamide, (2) N-[1-(3-amidino-phenyl)-2-(1H-tetrazol-5-yl)-ethyl]-3-methyl-4-(pyrrolidin-1-yl-carbonyl)-benzamide, (3) N-[1-(5-amidino-2-hydroxy-phenyl)-2-phenyl-ethyl]-3-methyl-4-(pyrrolidin-1-yl-carbonyl)-benzamide and (4) N-[1-(5-amidino-2-hydroxy-phenyl)-2-(pyridin-3-yl)-ethyl]-3-methyl-4-(pyrrolidin-1-yl-carbonyl)-benzamide, wherein the amidino group may additionally be substituted by a hydroxy, $C_{1-3}$-alkyloxy, $C_{1-8}$-alkoxy-carbonyl or phenylcarbonyl group, and the salts thereof.

According to the invention the compounds of general formula I are obtained by methods known per se, for example by the following methods:

a) In order to prepare a compound of formula I:
reacting a carboxylic acid of general formula

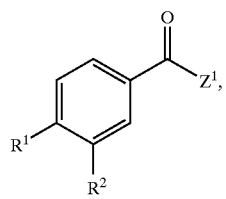

(II)

wherein
$R^1$ and $R^2$ are as hereinbefore defined and
$Z^1$ denotes a hydroxy group or a nucleofugic leaving group such as for example a $C_{1-6}$-alkoxy-carbonyloxy, $C_{1-6}$-alkyl-carbonyloxy or 2,6-dichlorophenylcarbonyloxy group or a chlorine or bromine atom,
or with an amine of general formula

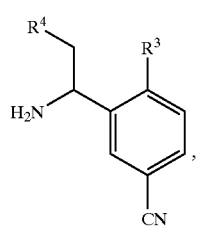

(III)

wherein $R^3$ and $R^4$ are as hereinbefore defined, while $R^3$ may optionally be protected during the reaction by a protective group, and subsequently converting the cyano compound thus obtained into an amidino compound.

The reaction is expediently carried out in a solvent such as methylene chloride, chloroform, carbon tetrachloride, ether, tetrahydrofuran, dioxane, benzene, toluene, acetonitrile, dimethylformamide or sulpholane, optionally in the presence of an inorganic or organic base at temperatures between −20 and 200° C., but preferably at temperatures between −10 and 160° C. The carboxylic acid derivative may be, for example, a corresponding halide or anhydride.

The reaction may be carried out with the free acid or an ester, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, triethylamine, N,N'-dicyclohexylcarbodiimide, N,N'-dicyclohexylcarbodiimide/N-hydroxysuccinimide or 1-hydroxy-benzotriazole, O-(benzotriazol-1-yl)-N,N,N',N'-tetramethyluronium tetrafluoroborate/N-methylmorpholine, propanephosphonic acid-cycloanhydride/N-methylmorpholine, N,N'-carbonyldiimidazole or N,N'-thionyldiimidazole or triphenylphosphine/carbon tetrachloride, at temperatures between −20 and 200° C., but preferably at temperatures between −10 and 160° C.

Other methods of amide coupling are described for example in P. D. Bailey, I. D. Collier, K. M. Morgan in Comprehensive Functional Group Interconversions Vol. 5, 257ff. Pergamon, 1995.

The subsequent conversion of the cyano group into an amidino group is carried out as described in process b).

b) In order to prepare a compound of general formula I wherein the amidino group is optionally substituted by a $C_{1-10}$-alkoxy-carbonyl, 2,2,2-trichloroethoxycarbonyl, phenyloxycarbonyl, benzyloxycarbonyl, phenylcarbonyl, hydroxy, $C_{1-5}$-alkyloxy, benzyloxy or phenyloxy group:

Reacting a Compound of General Formula

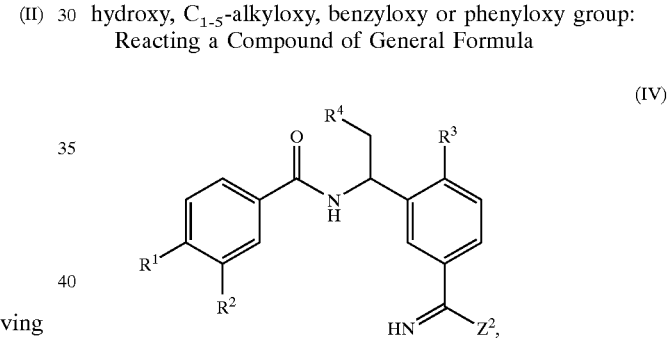

(IV)

optionally formed in the reaction mixture, wherein
$R^1$ to $R^4$ are as hereinbefore defined and
$Z^2$ denotes an alkoxy, aralkoxy, alkylthio or aralkylthio group, with an amine of general formula

H—$R^5NR^6$, (V)

wherein
$R^5$ denotes a hydrogen atom and
$R^6$ denotes a hydrogen atom or a hydroxy, $C_{1-5}$-alkyloxy, benzyloxy or phenyloxy group, or with the salts thereof.

The reaction is expediently carried out in a solvent such as methanol, ethanol, n-propanol, tetrahydrofuran or dioxane at temperatures between 0 and 150° C., preferably at temperatures between 0 and 80° C., with an amine of general formula V or with a corresponding acid addition salt such as for example ammonium carbonate or ammonium acetate.

A compound of general formula IV is obtained for example by reacting a corresponding cyano compound with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0 and 50° C., but preferably at 20° C., or a corresponding nitrile with hydrogen sulphide, conveniently in a solvent such as pyridine or dimethylformamide and in the presence of a base such as triethylamine, and subsequently alkylating the thioamide formed with a corresponding alkyl or aralkyl halide.

c) In order to prepare a compound of general formula I wherein $R^4$ denotes a tetrazoyl group:

Reacting a compound of general formula

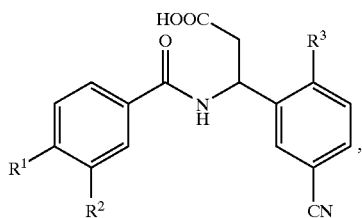

(VI)

prepared from a carboxylic acid and an amine according to process a), wherein $R^1$ to $R^3$ are as hereinbefore defined, first with an optionally substituted alkylcarboxylic acid nitrile such as for example 3-amino-propionic acid nitrile and then with sodium azide or trialkyl tin azide, subsequently cleaving the protective group with a suitable base and then converting the cyano compound thus obtained into an amidino compound.

The reaction with an optionally substituted alkylcarboxylic acid nitrile or with a salt thereof is conveniently carried out in the presence of coupling reagents such as O-(benzotriazol-1-yl)-N,N,N',N'-tetramethyluronium tetrafluoroborate or bases such as N-methylmorpholine or mixtures thereof in solvents such as for example dimethylformamide at temperatures between 10 and 30° C., preferably at ambient temperature. Other possible methods of amide coupling are also described in process a).

The reaction with sodium azide to form the protected tetrazole is conveniently carried out in a solvent such as acetonitrile at temperatures between 15 and 50° C., preferably at 40° C. Then trifluoromethanesulphonic acid anhydride is added at 0° C.

The cleaving of the protective group of the tetrazole with a suitable base is conveniently carried out in solvents such as for example dichloromethane at temperatures between 10 and 30° C., preferably at ambient temperature. An example of a suitable base is potassium tert. butoxide.

Other methods of preparing tetrazoles are described for example in H. R. Meier, H. Heimgartner in Houben-Weyl, vol. E8d Part 4, pp. 664 ff.

The subsequent conversion of the cyano group into an amidino group is carried out as described in process b).

If according to the invention a compound of general formula I is obtained which contains an amino or imino group, this may then be converted with a corresponding acyl-derivative into a corresponding acyl compound of general formula I and/or if a compound of general formula I is obtained which contains an esterified carboxy group, this may then be converted by hydrolysis into a corresponding carboxylic acid of general formula I and/or if a compound of general formula I is obtained which contains a carboxy group, this may then be converted by esterification into a corresponding ester.

The subsequent acylation is conveniently carried out with a corresponding halide or anhydride in a solvent such as methylene chloride, chloroform, carbon tetrachloride, ether, tetrahydrofuran, dioxane, benzene, toluene, acetonitrile or sulpholane, optionally in the presence of an inorganic or organic base at temperatures between –20 and 200° C., but preferably at temperatures between –10 and 160° C. However, it may also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/-N-hydroxysuccinimide or 1-hydroxy-benzotriazole, N,N'-carbonyldiimidazole or N,N'-thionyldiimidazole or triphenylphosphine/carbon tetrachloride, at temperatures between –20 and 200° C., but preferably at temperatures between –10 and 160° C. As a result of the acylation the $C_{1-10}$-alkoxy-carbonyl, 2,2,2-trichloroethoxycarbonyl, phenyloxycarbonyl, benzyloxycarbonyl or phenylcarbonyl group may be introduced, for example.

The subsequent hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane and the subsequent decarboxylation is carried out in the presence of an acid as hereinbefore described at temperatures between –10 and 120° C., e.g. at temperatures between ambient temperature and the boiling temperature of the reaction mixture.

The subsequent esterification is carried out with a corresponding alcohol, conveniently in a solvent or mixture of solvents such as methylene chloride, benzene, toluene, chlorobenzene, tetrahydrofuran, benzene/tetrahydrofuran or dioxane, but preferably in an excess of the alcohol used, optionally in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylamino-pyridine, conveniently at temperatures between 0 and 150° C., preferably at temperatures between 0 and 80° C., or with a corresponding halide in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously also serve as solvent, or optionally in the presence of silver carbonate or silver oxide at temperatures between –30 and 100° C., but preferably at temperatures between –10 and 80° C.

In the reactions described above any reactive group present such as hydroxy, carboxy, amino, alkylamino or imino groups may be protected during the reaction by conventional protecting groups which are cleaved again after the reaction.

For example, a suitable protecting group for a hydroxy group may be the methoxy, benzyloxy, trimethylsilyl, acetyl, benzoyl, tert.butyl, trityl, benzyl or tetrahydropyranyl group, suitable protecting groups for a carboxyl group might be the trimethylsilyl, methyl, ethyl, tert.butyl, benzyl or tetrahydropyranyl group, and suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

Other protecting groups and their cleaving are described in T. W. Greene, P. G. M. Wuts, Protective Groups in Synthesis, Wiley, 1991.

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is preferably cleaved hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

However, a 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)-chloride in a solvent such as aqueous ethanol and optionally in the presence of a base such as 1,4-diazabicyclo[2.2.2]octane at temperatures between 20 and 70° C.

The compounds of general formulae III to VI used as starting materials which are known from the literature are obtained by methods known from the literature and also their preparation is described in the Examples.

For example, a compound of general formula III may be prepared by reacting a compound of general formula

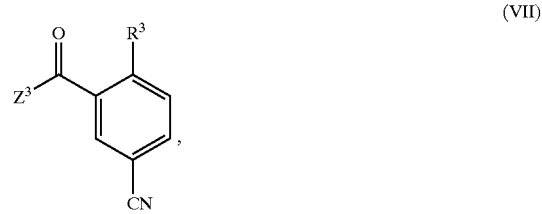

(VII)

wherein $R^3$ is as hereinbefore defined, $R^3$ optionally being protected prior to the reaction by a suitable protective group which is cleaved again after the reaction, and $Z^3$ denotes a leaving group such as for example a chlorine atom, with a compound of general formula

$R^4$—$CH_2$—$Z^4$ (VIII), wherein $R^4$ is as hereinbefore defined and $Z^4$ denotes a nucleofugic leaving group such as for example a chlorine, bromine or iodine atom or a p-tolylsulphonyl, methylsulphonyl or trifluoromethylsulphonyl group, in the presence of a catalyst such as for example tetrakis-triphenylphosphine-palladium(0) and zinc, and the resulting ketone is then converted with ammonium acetate in the presence of sodium cyanoborohydride and molecular sieve in the corresponding amine of general formula III. The alkylation is carried out for example in solvents such as tetrahydrofuran at temperatures between 10 and 30° C., preferably at ambient temperature. The subsequent conversion into the amine is conveniently carried out in solvents such as methanol, for example, at temperatures between 10 and 30° C., preferably at ambient temperature.

Alternatively, the starting compound of general formula III wherein $R^3$ denotes a hydroxy or amino group may be prepared by deprotonating a compound of general formula

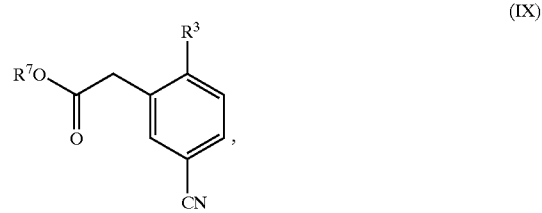

(IX)

wherein $R^3$ denotes an optionally protected hydroxy or amino group and $R^7OCO$ denotes an optionally protected carboxy group, while $R^7$ denotes hydrogen or a suitable protecting group such as for example a $C_{1-6}$-alkyl group, in the benzyl position and then alkylating by reacting with a compound of general formula

$R^4$—$CH_2$—$Z^4$ (X), wherein $R^4$ is as hereinbefore defined and $Z^4$ denotes a nucleofugic leaving group such as for example a chlorine, bromine or iodine atom or a p-tolylsulphonyl, methylsulphonyl or trifluoromethylsulphonyl group, and then converting the carboxylic acid derivative thus obtained into the corresponding amine. The deprotonation is carried out using suitable bases such as for example sodium hydride, potassium tert.butoxide or lithium diisopropylamine in solvents such as for example dimethylformamide, tetrahydrofuran, dimethylsulphoxide, ether or mixtures thereof at temperatures between −10 and 20° C., preferably 5 to 15° C. The conversion into the amine is carried out for example by reacting with diphenylphosphoric acid azide in solvents such as tert-butanol in the presence of bases such as triethylamine and potassium tert.butoxide at ambient temperature and subsequently treating with hydrochloric acid in a solvent such as dioxane at ambient temperature.

The preparation of carboxylic acid derivatives of general formula II is described in Methoden der organischen Chemie (Houben-Weyl), Volume E5, "Carboxylic acids and carboxylic acid derivatives", 4th edition, Verlag Thieme, Stuttgart 1985.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the new compounds of general formula I and the tautomers, the enantiomers, the diastereomers and the physiologically acceptable salts thereof have valuable pharmacological properties, particularly an antithrombotic effect which is preferably based on their influence on thrombin or factor Xa, for example a thrombin-inhibiting or factor Xa-inhibiting effect, on an aPTT time-prolonging effect and on an inhibiting effect on related serine proteases such as, for example, trypsin, urokinase, factor VIIa, factor IX, factor XI and factor XII.

For example the compounds (1) N-[1-(3-amidino-phenyl)-2-(1H-tetrazol-5-yl)-ethyl]-4-(2,5-dihydro-pyrrol-1-yl-carbonyl)-3-methyl-benzamide-hydrochloride and (2) N-[1-(3-amidino-phenyl)-2-(1H-tetrazol-5-yl)-ethyl]-3-methyl-4-(pyrrolidin-1-carbonyl)-benzamide-hydrochloride were investigated for their effect on the inhibition of factor Xa as follows:

Method: Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material

Tris(hydroxymethyl)-aminomethane buffer (100 mmol) and sodium chloride (150 mmol), pH 8.0

Factor Xa (Roche), spec. activity: 10 U/0.5 ml, final concentration: 0.175 U/ml for each reaction mixture Substrate Chromozym X (Roche), final concentration: 200 μMol/l for each reaction mixture Test substance: final concentration 100, 30, 10, 3, 1, 0.3, 0.1, 0.03, 0.01, 0.003, 0.001 μMol/l Procedure 10 μl of a 23.5-times concentrated starting solution of the test substance or solvent (control), 175 μl of tris (hydroxymethyl)-aminomethane buffer and 25 μl of a 1.65 U/ml Factor Xa working solution are incubated for 10 minutes at 37° C. After the addition of 25 μl of Chromozym X working solution (1.88 μmol/l) the sample is measured in a photometer (SpectraMax 250) at 405 nm for 150 seconds at 37° C.

Evaluation

1. Determining the maximum increase (deltaOD/minutes) over 3 measuring points.

2. Determining the % inhibition based on the solvent control.

3. Plotting a dosage/activity curve (% inhibition vs substance concentration).

4. Determining the $IC_{50}$ by interpolating the X-value (substance concentration) of the dosage/activity curve at Y=50% inhibition.

The Table that follows contains the results found:

| substance | inhibition of factor Xa (IC$_{50}$ in μM) |
|---|---|
| (1) | 0.008 |
| (2) | 0.026 |

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C)A), and occlusion in peripheral arterial diseases, and for the prevention and treatment of pulmonary embolism, disseminated intravascular coagulation, for preventing and treating coronary thrombosis, for preventing stroke and the occlusion of shunts. In addition, the compounds according to the invention are suitable for antithrombotic back-up in thrombolytic treatment, such as for example with alteplase, reteplase, tenecteplase, staphylokinase or streptokinase, for preventing long-term restenosis after PT(C)A, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with P$_2$T receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention without restricting its scope:

EXAMPLE 1

N-[1-(3-amidino-phenyl)-2-(1H-tetrazol-5-yl)-ethyl]-4-(2,5-dihydro-pyrrol-1-yl-carbonyl)-3-methyl-benzamide-hydrochloride a. 4-(2,5-dihydro-pyrrol-1-yl-carbonyl)-3-methyl-bromobenzene 25.0 g (0.12 mol) of 4-bromo-2-methylbenzoic acid are dissolved in 250 ml of dimethylformamide and after the addition of 41.7 g (0.13 mol) of O-(benzotriazol-1-yl)-N,N,N',N'-tetramethyluronium tetrafluoroborate, 14.3 ml (0.13 mol) of N-methylmorpholine and 9.6 ml (0.12 mol) of pyrrolidine the mixture is stirred for 16 hours at ambient temperature. Then it is poured onto ice water and extracted with ethyl acetate. The combined organic extracts are washed with sodium hydrogen carbonate solution, dried over sodium sulphate and concentrated by evaporation.

Yield: 31.6 g (97% of theory)

R$_f$ value: 0.45 (silica gel; dichloromethane/ethanol=19:1)

b. 4-(2,5-dihydro-pyrrol-1-yl-carbonyl)-3-methyl-benzonitrile 31.6 g (0.11 mol) of 4-(2,5-dihydro-pyrrol-1-yl-carbonyl)-3-methyl-bromobenzene are dissolved in 125 ml of dimethylformamide, and combined with 20.2 g (0.23 mol) of copper cyanide and 3.2 g (2.7 mmol) of tetrakis-triphenylphosphine-palladium-(0). The suspension is stirred for 20 hours at 140° C. Then it is cooled to 80° C., combined with 150 ml of water, 150 ml of ethyl acetate and 25 g Celite and filtered through Celite. The organic phase is separated off, washed with sodium chloride solution, dried over sodium sulphate and concentrated by evaporation. The residue is chromatographed on silica gel, eluting with ethyl acetate/ethanol (50:1 and 19:1).

Yield: 11.7 g (49% of theory)

R$_f$ value: 0.55 (silica gel; ethyl acetate/ethanol=9:1)

c. 4-(2,5-dihydro-pyrrol-1-yl-carbonyl)-3-methyl-benzoic acid 10.6 g (0.05 mol) of 4-(2,5-dihydro-pyrrol-1-yl-carbonyl)-3-methyl-benzonitrile are in 106 ml of ethanol and 106 ml 10 molar sodium hydroxide solution 30 minutes at 80° C. stirred. Then is the ethanol distilled off, the residue in water dissolved, über activated charcoal filtered and with 6 molar hydrochloric acid acidified. The ausgefallene acid is suction filtered and at 40° C. dried.

Yield: 7.5 g (64% der Therie)

R$_f$ value: 0.29 (silica gel; dichloromethane/ethanol=9:1)

d. ethyl 3-(3-cyanophenyl)-3-[4-(2,5-dihydro-pyrrol-1-yl-carbonyl)-3-methyl-benzoylamino]-propionate Prepared analogously to Example 1a from 4-(2,5-dihydro-pyrrol-1-yl-carbonyl)-3-methyl-benzoic acid, ethyl 3-amino-3-(3-cyanophenyl)-propionate, O-(benzotriazol-1-yl)-N,N,N',N'-tetramethyluronium tetrafluoroborate and N-methylmorpholine in dimethylformamide.

Yield: 70% of theory

R$_f$ value: 0.39 (silica gel; dichloromethane/ethanol=19:1)

e. 3-(3-cyanophenyl)-3-[4-(2,5-dihydro-pyrrol-1-yl-carbonyl)-3-methyl-benzoylamino]-propionic acid 4.0 g (9.3 mmol) of ethyl 3-(3-cyanophenyl)-3-[4-(2,5-dihydro-pyrrol-1-yl-carbonyl)-3-methyl-benzoylamino]-propionate are dissolved in 75 ml of ethanol and after the addition of 7.5 ml of 2 molar sodium hydroxide solution the mixture is stirred for 3 hours at ambient temperature. The ethanol is distilled off, the residue dissolved in water and acidified with 1 molar hydrochloric acid. The acid precipitated is suction filtered and dried at 40° C.

Yield: 3.4 g (91% of theory)

R$_f$ value: 0.28 (silica gel; dichloromethane/ethanol=9:1)

f. N-[1-(3-cyano-phenyl)-2-(2-cyano-ethylcarbamoyl)-ethyl]-4-(2,5-dihydro-pyrrol-1-yl-carbonyl)-3-methyl-benzamide Prepared analogously to Example 1a from 3-(3-cyanophenyl)-3-[4-(2,5-dihydro-pyrrol-1-yl-carbonyl)-3- methyl-benzoylamino]-propionic acid, 3-amino-propionic acid nitrile-fumarate, O-(benzotriazol-1-yl)-N,N,N',N'-tetramethyluronium tetrafluoroborate and N-methylmorpholine in dimethylformamide.

Yield: 44% of theory $R_f$ value: 0.45 (silica gel; dichloromethane/ethanol=9:1)

g. N-{1-(3-cyano-phenyl)-2-[1-(2-cyano-ethyl)-1H-tetrazol-5-yl]-ethyl}-4-(2,5-dihydro-pyrrol-1-yl-carbonyl)-3-methyl-benzamide 778 mg (1.7 mmol) of N-[1-(3-cyano-phenyl)-2-(2-cyano-ethylcarbamoyl)-ethyl]-4-(2,5-dihydro-pyrrol-1-yl-carbonyl)-3-methyl-benzamide are dissolved in 20 ml acetonitrile at 40° C., combined with 240 mg (3.7 mmol) of sodium azide and stirred for 10 minutes. Then at 0° C. 0.6 ml (3.7 mmol) of trifluoromethanesulphonic acid anhydride is added, the cooling bath is taken away and the mixture is stirred for another 20 minutes without cooling. Then ice water and sodium hydrogen carbonate solution are added and the mixture is extracted with ethyl acetate. The combined organic extracts are dried and concentrated by evaporation. The crude product is chromatographed on silica gel, eluting with dichloromethane/ethanol (50:1 to 19.1).

Yield: 175 mg (21% of theory)

$R_f$ value: 0.5 (silica gel; dichloromethane/ethanol=9:1)

h. N-[1-(3-cyano-phenyl)-2-(1H-tetrazol-5-yl)-ethyl]-4-(2,5-dihydro-pyrrol-1-yl-carbonyl)-3-methyl-benzamide 510 mg (1 mmol) of N-{1-(3-cyano-phenyl)-2-[1-(2-cyano-ethyl)-1H-tetrazol-5-yl]-ethyl}-4-(2,5-dihydro-pyrrol-1-yl-carbonyl)-3-methyl-benzamide are dissolved in 75 ml dichloromethane and after the addition of 380 mg (3.4 mmol) of potassium tert. butoxide the mixture is stirred for 2 hours at ambient temperature. The solvent is distilled off, the residue is combined with ice water, adjusted to pH 4 with glacial acetic acid and extracted with ethyl acetate. The combined organic extracts are concentrated by evaporation. The residue is recrystallised from ether/petroleum ether 1:1.

Yield: 420 mg (93% of theory)

$R_f$ value: 0.25 (silica gel; dichloromethane/ethanol/glacial acetic acid=4:1:0.1)

i. N-[1-(3-amidino-phenyl)-2-(1H-tetrazol-5-yl)-ethyl]-4-(2,5-dihydro-pyrrol-1-yl-carbonyl)-3-methyl-benzamide-hydrochloride 415 mg (0.97 mmol) of N-[1-(3-cyano-phenyl)-2-(1H-tetrazol-5-yl)-ethyl]-4-(2,5-dihydro-pyrrol-1-yl-carbonyl)-3-methyl-benzamide are dissolved in 25 ml of saturated ethanolic hydrochloric acid and stirred for 7 hours at ambient temperature. The solvent is distilled off, the residue is dissolved in 20 ml of absolute ethanol and combined with 1.0 g (10.4 mmol) of ammonium carbonate. After 16 hours the precipitate formed is suction filtered, stirred with water, suction filtered again and dried.

Yield: 0.23 g (49% of theory)

$R_f$ value: 0.25 (silica gel; dichloromethane/ethanol/glacial acetic acid=4:1:0.1)

$C_{23}H_{24}N_8O_2 \times HCl$ (444.49/480.96)

| Mass spectrum: | $(M + H)^+$ = | 445 |
|---|---|---|
|  | $(M - H)^-$ = | 443 |

EXAMPLE 2

N-[1-(3-amidino-phenyl)-2-(1H-tetrazol-5-yl)-ethyl]-3-methyl-4-(pyrrolidin-1-yl-carbonyl)-benzamide-hydrochloride 125 mg (0.26 mmol) of N-[1-(3-amidino-phenyl)-2-(1H-tetrazol-5-yl)-ethyl]-4-(2,5-dihydro-pyrrol-1-yl-carbonyl)-3-methyl-benzamide-hydrochloride are dissolved in 25 ml of methanol and after the addition of 50 mg palladium on activated charcoal hydrogenated with hydrogen at ambient temperature. Then the catalyst is filtered off and the filtrate is concentrated by evaporation. The residue is recrystallised from ether/ethyl acetate/petroleum ether 1:1:1.

Yield: 63 mg (50% of theory)

$R_f$ value: 0.25 (silica gel; dichloromethane/ethanol/glacial acetic acid=4:1:0.1)

$C_{23}H_{26}N_8O_2 \times HCl$ (446.49/480.96)

| Mass spectrum: | $(M + H)^+$ = | 447 |
|---|---|---|
|  | $(M - H)^-$ = | 445 |

EXAMPLE 3

N-[1-(5-amidino-2-hydroxy-phenyl)-2-phenyl-ethyl]-3-methyl-4-(pyrrolidin-1-yl-carbonyl)-benzamide-hydrochloride a. (2-benzyloxy-5-cyano-phenyl)-acetic acid 6.3 g (19.6 mmol) of (2-benzyloxy-5-bromo-phenyl)-acetic acid, 2.9 g (32.9 mmol) of copper-(I)-cyanide, 0.45 g (0.39 mmol) of tetrakis-triphenylphosphine-palladium-(0) and 4.8 g aluminium oxide N are stirred in 30 ml of dimethylformamide for 13 hours at 140° C. After standing overnight the insoluble matter is filtered off and the solution is concentrated by evaporation. The residue is distributed in ethyl acetate/1 molar hydrochloric acid, the combined organic extracts are dried and concentrated by evaporation. The crude product is chromatographed on silica gel, eluting with dichloromethane.

Yield: 2.6 g (49% of theory)

$R_f$ value: 0.45 (silica gel; dichloromethane/ethanol=95:5)

b. methyl (2-benzyloxy-5-cyano-phenyl)-acetate 10.0 g (0.037 mol) of (2-benzyloxy-5-cyano-phenyl)-acetic acid are refluxed for two hours in 65 ml dichloromethane, 0.1 ml of dimethylformamide and 8.1 ml (0.11 mol) of thionyl chloride. Then the mixture is concentrated by evaporation, the residue is combined with 55 ml of methanol and refluxed for one hour. After cooling the mixture is suction filtered, washed with ether/petroleum ether and dried at 50° C.

Yield: 7.8 g (75% of theory)

melting point: 100° C.

c. methyl 2-(2-benzyloxy-5-cyano-phenyl)-3-phenyl-propionate 4.6 g (16.3 mmol) of methyl (2-benzyloxy-5-cyano-phenyl)-acetate are dissolved in 10 ml of dimethylformamide and 1.9 g (17 mmol) of potassium tert. butoxide are added. Then 2 ml (16.8 mmol) of benzylbromide are added dropwise while cooling gently with ice and the mixture is then stirred for another two hours at ambient temperature. It is stirred with ice water and extracted with ethyl acetate. The combined organic extracts are dried and concentrated by evaporation. The crude product is chromatographed on silica gel, eluting with petroleum ether/ethyl acetate (0–7%).

Yield: 4.8 g (79% of theory)

$R_f$ value: 0.45 (silica gel; petroleum ether/ethyl acetate=4:1)

d. 2-(2-benzyloxy-5-cyano-phenyl)-3-phenyl-propionic acid

Prepared analogously to Example 1e from methyl 2-(2-benzyloxy-5-cyano-phenyl)-3-phenyl-propionate and sodium hydroxide solution in methanol.

Yield: 95% of theory $R_f$ value: 0.3 (Reversed phase RP 8; 5% sodium chloride solution/methanol=1:3)

melting point: 169–171° C.

e. tert.butyl N-[1-(2-benzyloxy-5-cyano-phenyl)-2-phenyl-ethyl]-carbaminate

A suspension of 3.5 g (9.7 mmol) of 2-(2-benzyloxy-5-cyano-phenyl)-3-phenyl-propionic acid in 35 ml tert.butanol is combined with 1.4 ml (9.8 mmol) of triethylamine and 2.2 ml (9.8 mmol) of phosphoric acid diethylester azide and refluxed for 2.5 hours. Then the mixture is cooled to ambient temperature, combined with 0.87 g (7.8 mmol) of potassium tert. butoxide and stirred for one hour. It is then combined with ice water, suction filtered and the residue is chromatographed on silica gel, eluting with dichloromethane/methanol/1% ammonia 0–5%.

Yield. 2.2 g (52% of theory)

$R_f$ value: 0.6 (silica gel; petroleum ether/ethyl acetate/ammonia=4:1:0.1)

f. 3-(1-amino-2-phenyl-ethyl)-4-benzyloxy-benzonitrile 1.5 g (3.5 mmol) of tert.butyl N-[1-(2-benzyloxy-5-cyano-phenyl)-2-phenyl-ethyl]-carbaminate are suspended in 30 ml dioxane and 25 ml of tetrahydrofuran and after the addition of 45 ml of 6 molar hydrochloric acid stirred at ambient temperature over the weekend. Then it is diluted with ice water and extracted with ether. The aqueous phase is made alkaline with conc. ammonia and extracted with ethyl acetate. The combined organic extracts are dried with sodium sulphate and concentrated by evaporation.

Yield: 0.88 g (77% of theory)

$R_f$ value: 0.5 (silica gel; petroleum ether/ethyl acetate/ammonia=1:1:0.1)

g. N-[1-(2-benzyloxy-5-cyano-phenyl)-2-phenyl-ethyl]-3-methyl-4-(pyrrolidin-1-yl-carbonyl)-benzamide Prepared analogously to Example 1d from 4-(pyrrolidin-1-yl-carbonyl)-3-methyl-benzoic acid, 3-(1-amino-2-phenyl-ethyl)-4-benzyloxy-benzonitrile, O-(benzotriazol-1-yl)-N,N,N',N'-tetramethyluronium tetrafluoroborate and N-methylmorpholine in dimethylformamide.

Yield: 67% of theory $R_f$ value: 0.7 (silica gel; ethyl acetate plus 1% ammonia)

h. N-[1-(5-amidino-2-benzyloxy-phenyl)-2-phenyl-ethyl]-3-methyl-4-(pyrrolidin-1-yl-carbonyl)-benzamide-dihydrochloride Prepared analogously to Example 1i from N-[1-(2-benzyloxy-5-cyano-phenyl)-2-phenyl-ethyl]-3-methyl-4-(pyrrolidin-1-yl-carbonyl)-benzamide and hydrochloric acid/ammonium carbonate in ethanol.

Yield: 99% of theory $R_f$ value: 0.35 (Reversed phase RP 8; 5% sodium chloride solution/methanol=1:3)

i. N-[1-(5-amidino-2-hydroxy-phenyl)-2-phenyl-ethyl]-3-methyl-4-(pyrrolidin-1-yl-carbonyl)-benzamide-hydrochloride Prepared analogously to Example 2 from N-[1-(5-amidino-2-benzyloxy-phenyl)-2-phenyl-ethyl]-3-methyl-4-(pyrrolidin-1-yl-carbonyl)-benzamide-dihydrochloride and palladium on activated charcoal in methanol.

Yield: 96% of theory $R_f$ value: 0.70 (Reversed phase RP 8; 5% sodium chloride solution/methanol=1:3)

$C_{28}H_{30}N_4O_3 \times HCl$ (470.57/507.03)

Mass spectrum: $(M+H)^+$=471

EXAMPLE 4

N-[1-(5-amidino-2-hydroxy-phenyl)-2-(pyridin-3-yl)-ethyl]-3-methyl-4-(pyrrolidin-1-yl-carbonyl)-benzamide Prepared analogously to Example 2 from N-[1-(5-amidino-2-benzyloxy-phenyl)-2-(pyridin-3-yl)-ethyl]-3-methyl-4-(pyrrolidin-1-yl-carbonyl)-benzamide-hydrochloride and palladium on activated charcoal in methanol.

Yield: 47% of theory $R_f$ value: 0.5 (Reversed phase RP 8; 5% sodium chloride solution/methanol=2:3)

$C_{27}H_{29}N_5O_3$ (471.56)

Mass spectrum: $(M+H)^+$=472

EXAMPLE 5

Dry Ampoule Containing 75 mg of Active Substance per 10 ml

| Composition: | |
|---|---|
| Active substance | 75.0 mg |
| Mannitol | 50.0 mg |
| water for injections | ad 10.0 ml |

Preparation

Active substance and mannitol are dissolved in water. After packaging the solution is freeze-dried. To produce the solution ready for use, the product is dissolved in water for injections.

EXAMPLE 6

Dry Ampoule Containing 35 mg of Active Substance per 2 ml

| Composition: | |
|---|---|
| Active substance | 35.0 mg |
| Mannitol | 100.0 mg |
| water for injections | ad 2.0 ml |

Preparation

Active substance and mannitol are dissolved in water. After packaging, the solution is freeze-dried.

To produce the solution ready for use, the product is dissolved in water for injections.

EXAMPLE 7

Tablet Containing 50 mg of Active Substance

| Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
|  | 215.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 8
Tablet Containing 350 mg of Active Substance

| Composition: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 9
Capsules Containing 50 mg of Active Substance

| Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation (1) is triturated with (3). This trituration is added to the mixture of (2) and (4) with vigorous mixing.

This powder mixture is packed into size 3 hard gelatine capsules in a capsule filling machine.

EXAMPLE 10
Capsules Containing 350 mg of Active Substance

| Composition: | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation (1) is triturated with (3). This trituration is added to the mixture of (2) and (4) with vigorous mixing.

This powder mixture is packed into size 0 hard gelatine capsules in a capsule filling machine.

EXAMPLE 11
Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |

-continued

| 1 suppository contains: | |
|---|---|
| Polyethylenesorbitan monostearate | 840.0 mg |
| | 2000.0 mg |

Preparation

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula I

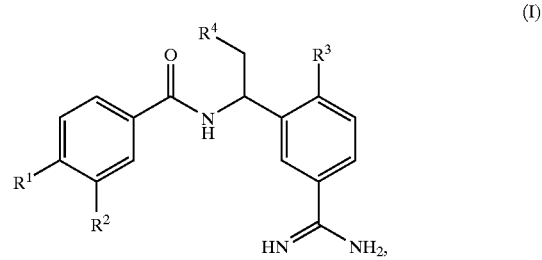

wherein:

$R^1$ denotes an amino, $C_{1-5}$-alkylamino, $C_{3-7}$-cycloalkylamino or (phenyl-$C_{1-3}$-alkyl)-amino group which may be substituted in each case at the amino-nitrogen atom by a phenylcarbonyl or phenylsulphonyl group or by a $C_{1-3}$-alkyl or $C_{1-3}$-alkyl-carbonyl group optionally substituted in the alkyl moiety by a carboxy group, a group which may be converted in-vivo into a carboxy group, an amino, $C_{1-3}$-alkylamino or di-($C_{1-3}$-alkyl)-amino group, while two nitrogen atoms are separated from each other by at least two carbon atoms, a di-($C_{1-5}$-alkyl)amino or N—($C_{3-7}$-cycloalkyl)-$C_{1-5}$-alkylamino group, while the $C_{1-5}$-alkyl moiety may be substituted in each case by a hydroxy, $C_{1-3}$-alkoxy, amino, $C_{1-3}$-alkyl-amino or di-($C_{1-3}$-alkyl)-amino group, with the exception of the 1 position, a 4- to 7-membered cycloalkyleneiminocarbonyl or cycloalkyleneiminosulphonyl group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylamino-carbonyl or di-($C_{1-3}$-alkyl)-aminocarbonyl group, a 2,5-dihydro-1H-pyrrol-1-yl-carbonyl group, an aminosulphonyl group optionally substituted by one or two $C_{1-3}$-alkyl groups, a $C_{3-7}$-cycloalkyl-carbonyl group, while
  the methylene group in the 3 or 4 position of a $C_{5-7}$-cycloalkyl-carbonyl group may be replaced by a —NH group wherein
    the hydrogen atom of the —NH group may be replaced by a $C_{1-3}$-alkyl or $C_{1-3}$-alkyl-carbonyl group, a phenylcarbonyl or heteroarylcarbonyl group,
  which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl or a 4- to 7-membered cycloalkyleneimino group,
  while the phenyl moiety may be substituted by a fluorine, chlorine or bromine atom, by a trifluoromethyl, $C_{1-3}$-alkyl, amino-$C_{1-3}$-alkyl, $C_{1-3}$-alkyl-amino-$C_{1-3}$-alkyl, di-($C_{1-3}$-alkyl)-amino-$C_{1-3}$-alkyl or $C_{1-3}$-alkoxy group,
or a group of formula

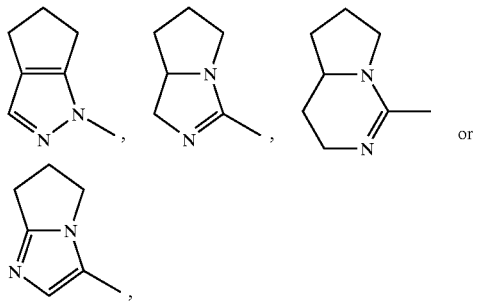

wherein in the heterocyclic moiety a hydrogen atom may be replaced by an aminomethyl or aminocarbonyl group in each case,
$R^2$ denotes a hydrogen, fluorine, chlorine or bromine atom, a $C_{1-3}$-alkyl group wherein the hydrogen atoms may be wholly or partially replaced by fluorine atoms, a $C_{2-3}$-alkenyl, $C_{1-3}$-alkoxy or trifluoromethoxy group,
$R^3$ denotes a hydrogen atom or a hydroxy or amino group and
$R^4$ denotes a phenyl or heteroaryl group which is optionally substituted by a hydroxy, $C_{1-4}$-alkyloxy, benzyloxy, hydroxycarbonyl-$C_{1-3}$-alkoxy, $C_{1-3}$-alkyloxy-carbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, carboxy, $C_{1-3}$-alkyloxy-carbonyl group,
a 1-H-pyridonyl or 1-($C_{1-3}$-alkyl)-pyridonyl group,
a 4- to 7-membered cycloalkyleneimino group or
a 4- to 7-membered cycloalkyl group wherein one or two methylene groups are replaced by an —NH or —N($C_{1-3}$-alkyl)- group and wherein one or two of the methylene groups adjacent to the —NH or —N($C_{1-3}$-alkyl)- group may each be replaced by a carbonyl group, with the proviso that a cycloalkyl group as hereinbefore defined wherein two —NH or —N($C_{1-3}$-alkyl)- groups are separated from one another by precisely one —CH$_2$— group is excluded,
while, unless otherwise stated, the term heteroaryl group denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
  the 6-membered heteroaryl group contains one, two or three nitrogen atoms and
  the 5-membered heteroaryl group contains an imino group optionally substituted by a $C_{1-3}$-alkyl or phenyl-$C_{1-3}$-alkyl group, an oxygen or sulphur atom or
  contains an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or phenyl-$C_{1-3}$-alkyl group or an oxygen or sulphur atom and additionally contains a nitrogen atom or contains an imino group optionally substituted by a $C_{1-3}$-alkyl or phenyl-$C_{1-3}$-alkyl group and two or three nitrogen atoms,
  and moreover a phenyl ring may be fused to the abovementioned monocyclic heterocyclic groups via two adjacent carbon atoms and the binding takes place via a nitrogen atom or via a carbon atom of the heterocyclic moiety or a fused-on phenyl ring,
while the amidino group contained in the compounds of general formula I may be substituted by a $C_{1-10}$-alkoxycarbonyl, 2,2,2-trichloroethoxycarbonyl, phenyloxycarbonyl, benzyloxycarbonyl, phenylcarbonyl, hydroxy, $C_{1-5}$-alkyloxy, benzyloxy or phenyloxy group,
and while the abovementioned alkyl and alkoxy groups include straight-chain and branched alkyl and alkoxy groups, wherein additionally one to 3 hydrogen atoms may be replaced by fluorine atoms,
or a tautomer or pharmaceutically acceptable salt thereof.

2. A compound of the formula I according to claim 1, wherein
$R^2$, $R^3$ and $R^4$ are defined as in claim 1 and
$R^1$ denotes a 4- to 7-membered cycloalkyleneiminocarbonyl group optionally substituted by a $C_{1-3}$-alkyl, amino-$C_3$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylamino-carbonyl or di-($C_{1-3}$-alkyl)-aminocarbonyl group,
a 2,5-dihydro-1H-pyrrol-1-ylcarbonyl group or
a group of formula

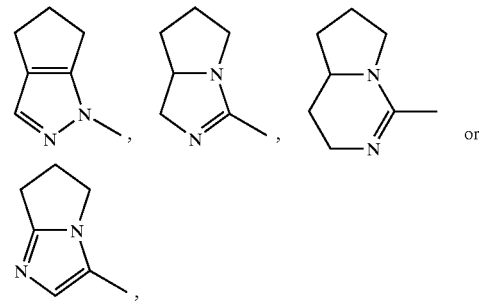

wherein in the heterocyclic moiety a hydrogen atom may be replaced in each case by an aminomethyl or aminocarbonyl group,
while the amidino group contained in the compounds of general formula I may be substituted by a $C_{1-10}$-alkoxycarbonyl, 2,2,2-trichloroethoxycarbonyl, phenyloxycarbonyl, benzyloxycarbonyl, phenylcarbonyl, hydroxy, $C_{1-5}$-alkyloxy, benzyloxy or phenyloxy group,
the abovementioned alkyl and alkoxy groups including straight-chain and branched alkyl and alkoxy groups, wherein additionally one to 3 hydrogen atoms may be replaced by fluorine atoms,
or a tautomer or pharmaceutically acceptable salt thereof.

3. A compound of the formula I according to claim 2, wherein
$R^1$, $R^2$ and $R^3$ are defined as in claim 2 and
$R^4$ denotes a phenyl, furanyl, thienyl, pyrrolyl, pyrazolyl, pyridinyl, pyrazinyl, pyridazinyl, pyrimidinyl, thiazolyl, tetrazolyl or isoxazolyl group which is optionally substituted by a hydroxy, $C_{1-4}$-alkyloxy, benzyloxy, hydroxycarbonyl-$C_{1-3}$-alkoxy, $C_{1-3}$-alkyloxy-carbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, carboxy, $C_{1-3}$-alkyloxy-carbonyl group, while the amidino group contained in the compounds of general formula I may be substituted by a $C_{1-10}$-alkoxy-carbonyl, 2,2,2-trichloroethoxycarbonyl, phenyloxycarbonyl, benzyloxycarbonyl, phenylcarbonyl, hydroxy, $C_{1-5}$-alkyloxy, benzyloxy or phenyloxy group, the abovementioned alkyl and alkoxy groups including straight-chain and branched alkyl and alkoxy groups, wherein additionally one to 3 hydrogen atoms may be replaced by fluorine atoms, or a tautomer or pharmaceutically acceptable salt thereof.

4. A compound selected from the group consisting of:
 (a) N-[1-(3-amidino-phenyl)-2-(1H-tetrazol-5-yl)-ethyl]-4-(2,5-dihydro-pyrrol-1-yl-carbonyl)-3-methyl-benzamide,
 (b) N-[1-(3-amidino-phenyl)-2-(1H-tetrazol-5-yl)-ethyl]-3-methyl-4-(pyrrolidin-1-yl-carbonyl)-benzamide,
 (c) N-[1-(5-amidino-2-hydroxy-phenyl)-2-phenyl-ethyl]-3-methyl-4-(pyrrolidin-1-yl-carbonyl)-benzamide, and
 (d) N-[1-(5-amidino-2-hydroxy-phenyl)-2-(pyridin-3-yl)-ethyl]-3-methyl-4-(pyrrolidin-1-yl-carbonyl)-benzamide, or an analog of compound (a), (b) or (c) wherein the amidino group is substituted by a hydroxy, $C_{1-3}$-alkyloxy, $C_{1-8}$-alkoxy-carbonyl or phenylcarbonyl group, or a pharmaceutically acceptable salt thereof.

5. A pharmaceutical composition comprising a compound in accordance with claim 1, 2, 3 or 4 together with one or more inert carriers and/or diluents.

6. A method for treating or inhibiting thrombus formation which comprises administering to a host in need of antithrombotic treatment or at risk of thrombus formation inhibition an antithrombotic amount of a compound in accordance with claim 1, 2, 3 or 4.

* * * * *